(12) United States Patent
Duffy et al.

(10) Patent No.: US 8,617,883 B2
(45) Date of Patent: Dec. 31, 2013

(54) MESENCHYMAL STEM CELL FOR PROMOTING NEOVASCULARISATION

(75) Inventors: Garry Paul Duffy, Galway (IE); Frank Barry, Galway (IE); Timothy O'Brien, Galway (IE)

(73) Assignee: National University of Ireland, Galway, Galway (IE)

( * ) Notice: Subject to any disclaimer, the term of this patent is extended or adjusted under 35 U.S.C. 154(b) by 852 days.

(21) Appl. No.: 12/183,992

(22) Filed: Jul. 31, 2008

(65) Prior Publication Data
US 2010/0028401 A1 Feb. 4, 2010

(51) Int. Cl.
*C12N 5/08* (2006.01)

(52) U.S. Cl.
USPC ........................................................ 435/372

(58) Field of Classification Search
None
See application file for complete search history.

(56) References Cited

U.S. PATENT DOCUMENTS

| | | |
|---|---|---|
| 2003/0157078 A1 | 8/2003 | Hall et al. |
| 2005/0019911 A1 | 1/2005 | Gronthos et al. |
| 2005/0249731 A1 | 11/2005 | Aslan et al. |
| 2009/0004661 A1* | 1/2009 | Shetty et al. ............... 435/6 |

OTHER PUBLICATIONS

Yuan K et al., J. Periodontal Res., 2000, v.35, pp. 165-171.*
Delorme et al., Methods in Molecular Medicine, 2007,v.140, pp. 67-81.*
Aslan et al. (2007) "Nucleofection-based ex vivo nonviral gene delivery to human stem cells as a platform for tissue regeneration," *Tissue Eng*, 12:877-889.
Barry and Murphy (2004) "Mesenchymal stem cells: clinical applications and biological characterization," *Int J Biochem Cell Biol*, 36(4):568-584.
Dzau et al. (2005) "Enhancing stem cell therapy through genetic modification," *J Am Coll Cardiol*, 46:1351-1353.
Haleem-Smith et al. (2005) "Optimization of high-efficiency transfection of adult human mesenchymal stem cells in vitro," *Mol Biotechnol*, 30:9-20.
Jaiswal et al. (1997) "Osteogenic differentiation of purified, culture-expanded human mesenchymal stem cells in vitro," *J Cell Biochem*, 64:295-312.
Jones et al. (2002) "Isolation and characterization of bone marrow multipotential mesenchymal progenitor cells," *Arthritis Rheum*, 46(12):3349-3360.
Lin et al. (2003) "In vitro culture of human bone marrow mesenchymal stem cell colonies and induced differentiation into neuron-like cells." Di Yi Jun Yi Da Xue Xue Bao, 23(3):251-3, 264.
Månsson-Broberg et al. (2008) "Modulation of ephrinB2 leads to increased angiogenesis in ischemic myocardium and endothelial cell proliferation," *Biochem Biophys Res Commun* 373(3):355-359.
Murphy et al. (2003) "Stem cell therapy in a caprine model of osteoarthritis," *Arthritis Rheum*, 48:3464-3474.
Xu et al. (2008) "EphrinB2 gene transfection promotes the differentiation of bone marrow mesenchymal stem cells into vascular endothelial cells," *J South Med Univ* 28(5):790-794. (English title and abstract only).
Yang et al. (2007) "Effects of myocardial transplantation of marrow mesenchymal stem cells transfected with vascular endothelial growth factor for the improvement of heart function and angiogenesis after myocardial infarction," *Cardiology* 107:17-29.
Yau et al. (2007) "Enhanced angiogenesis with multimodal cell-based gene therapy," *Ann Thorac Surg*, 83:1110-1119.

* cited by examiner

*Primary Examiner* — Michail Belyavskyi
(74) *Attorney, Agent, or Firm* — Foley & Lardner LLP; Antoinette F. Konski

(57) ABSTRACT

The Eph (erythropoietin-producing hepatocellular carcinoma) receptors and their cell surface anchored ligands, the Ephrins, comprise the largest of the receptor tyrosine kinases families with 14 receptors and 8 ligands. The receptors are subdivided into Eph-A and Eph-B categories and have known actions in the development of the vascular and nervous system. The present invention relates to an isolated mesenchymal stem cell selected from the group consisting of an isolated mesenchymal stem cell that expresses Ephrin-B2, an isolated mesenchymal stem cell that over-expresses Ephrin-B2, and an isolated mesenchymal stem cell that is genetically modified to increase Ephrin-B2 expression. The invention further relates to the various applications of the isolated mesenchymal stem cells of the present invention.

5 Claims, 17 Drawing Sheets

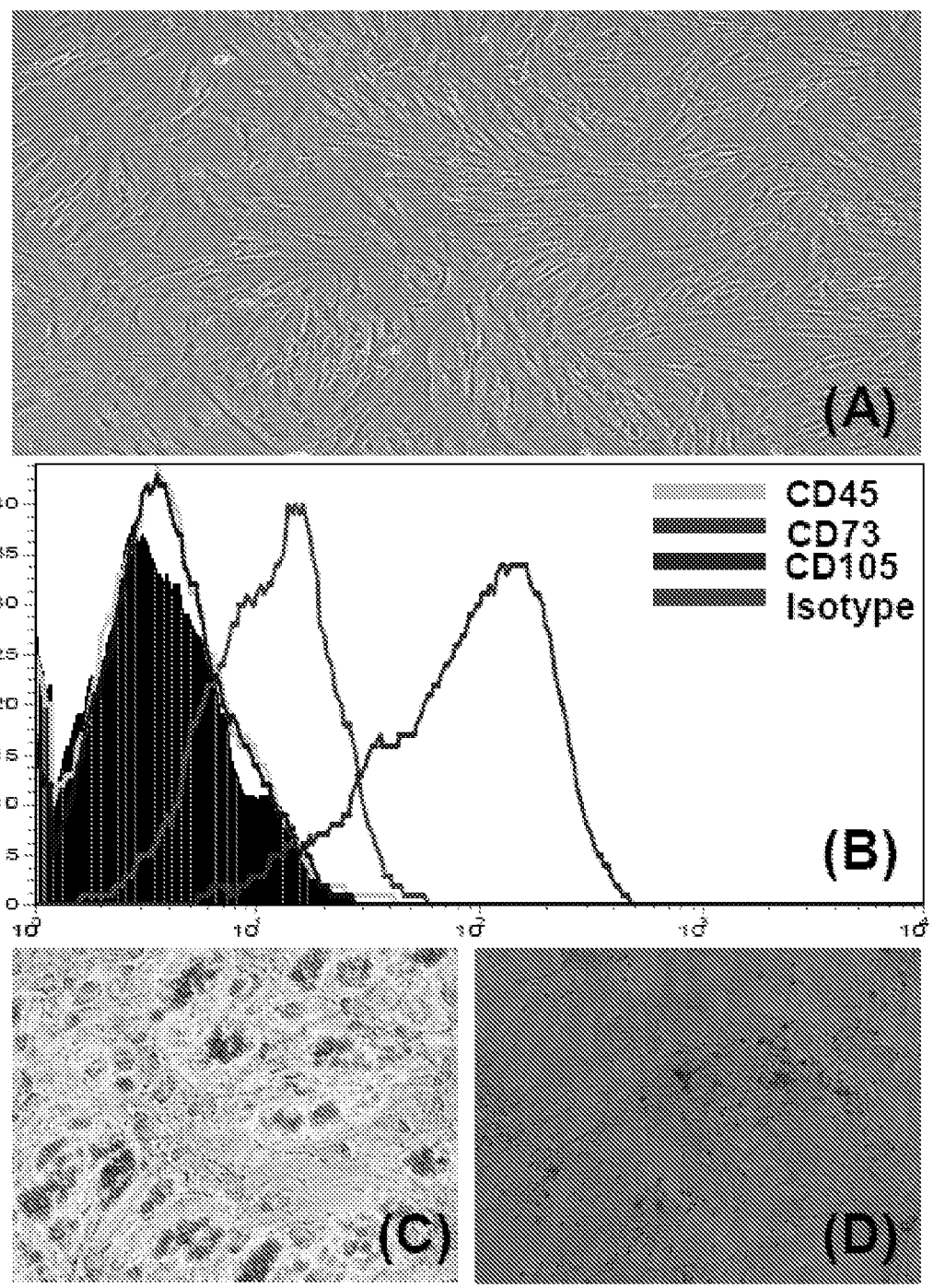
Figure 1(A),(B),(C),(D)

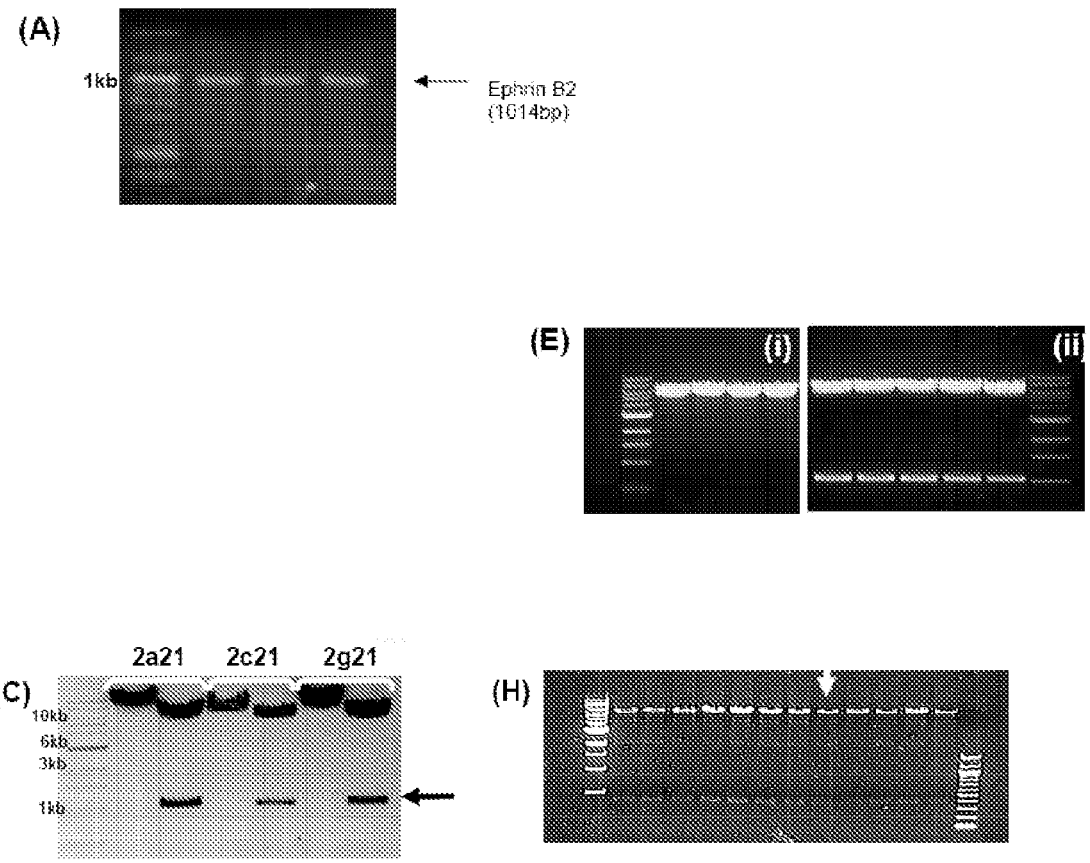
Figure 2(A),(C),(E),(H)

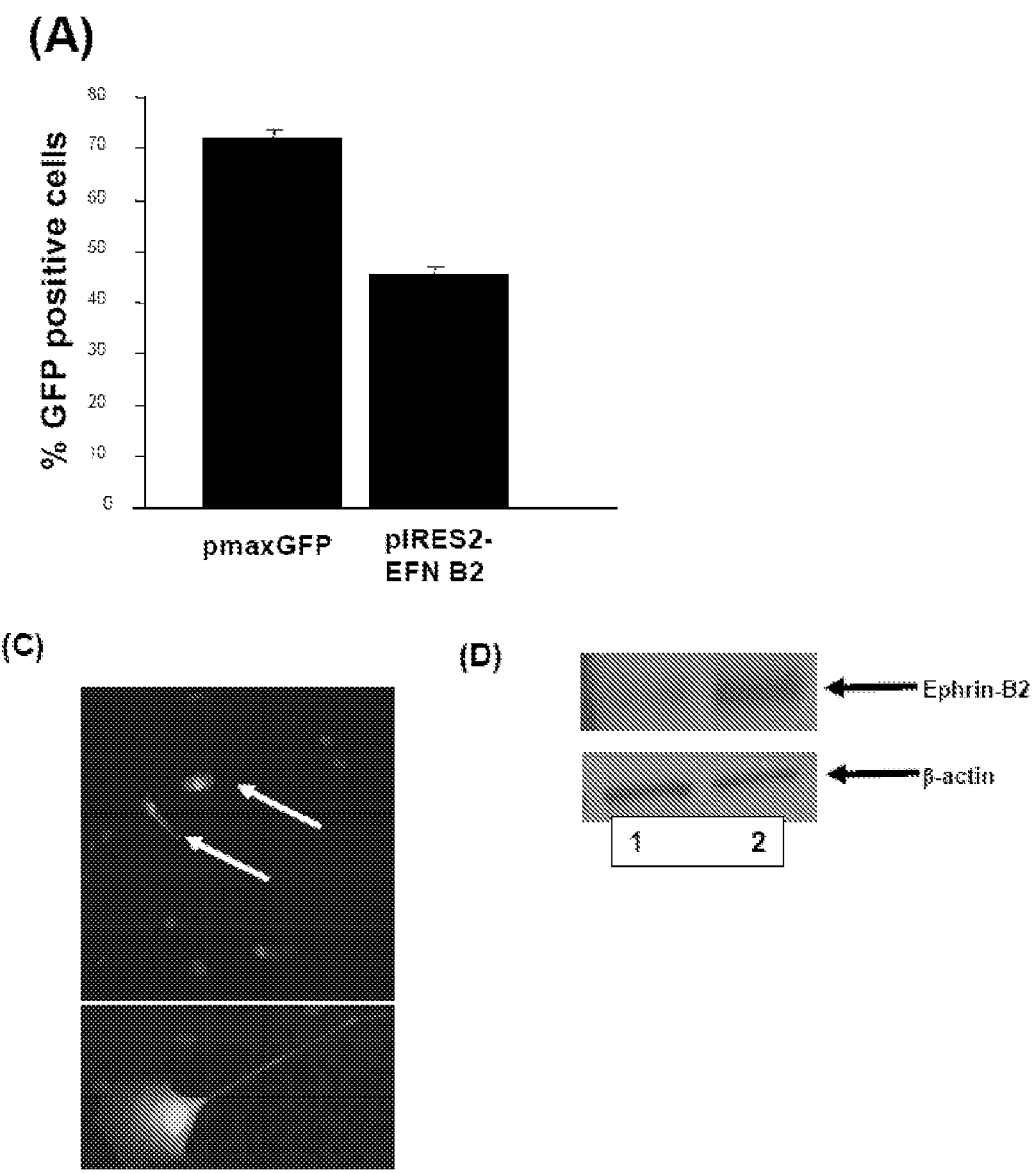
Figure 3(A),(C),(D)

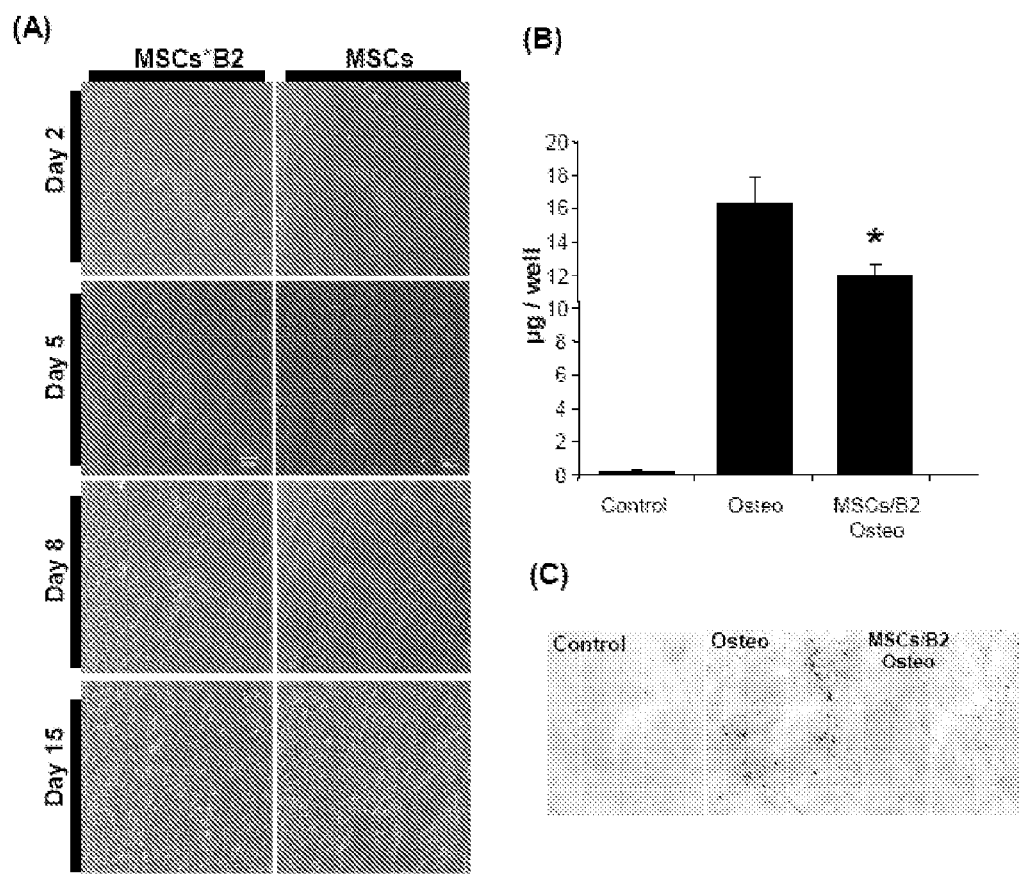
Figure 5(A),(B),(C)

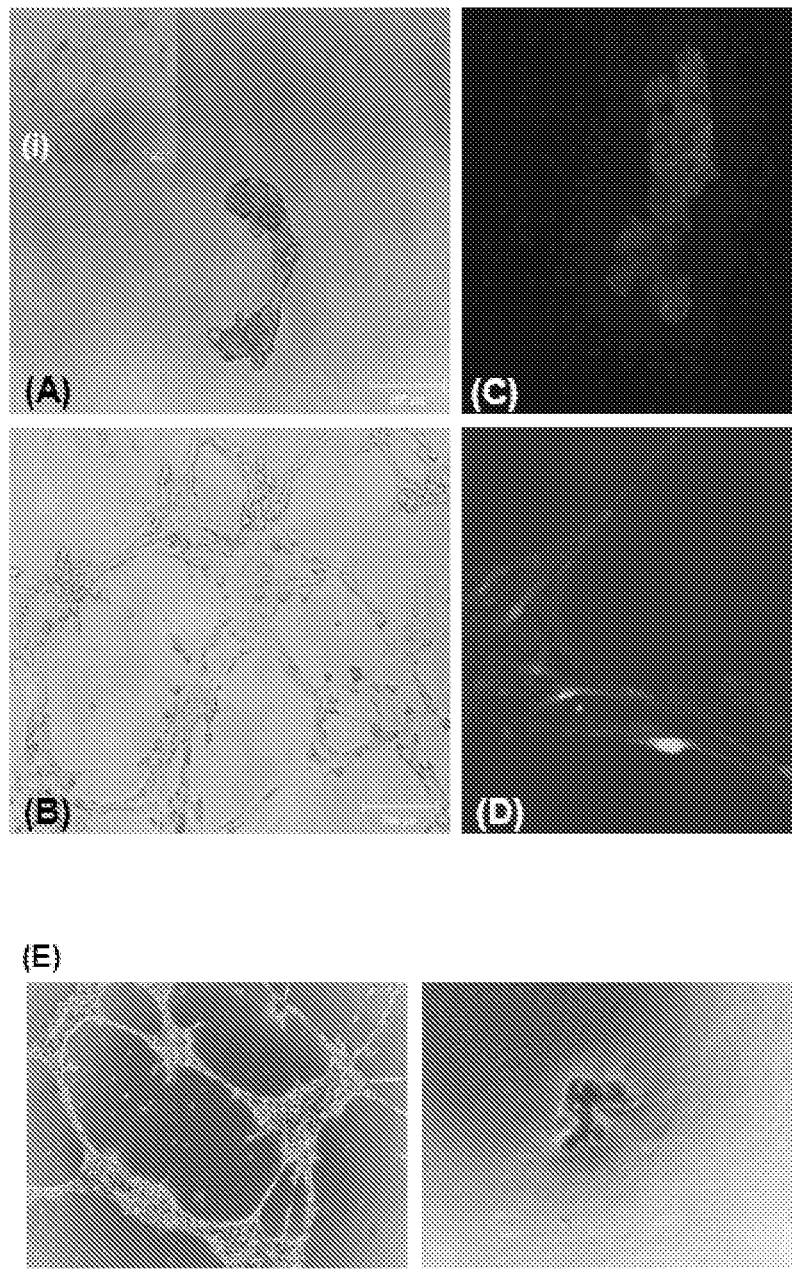
Figure 6(A),(B),(C),(D),(E)

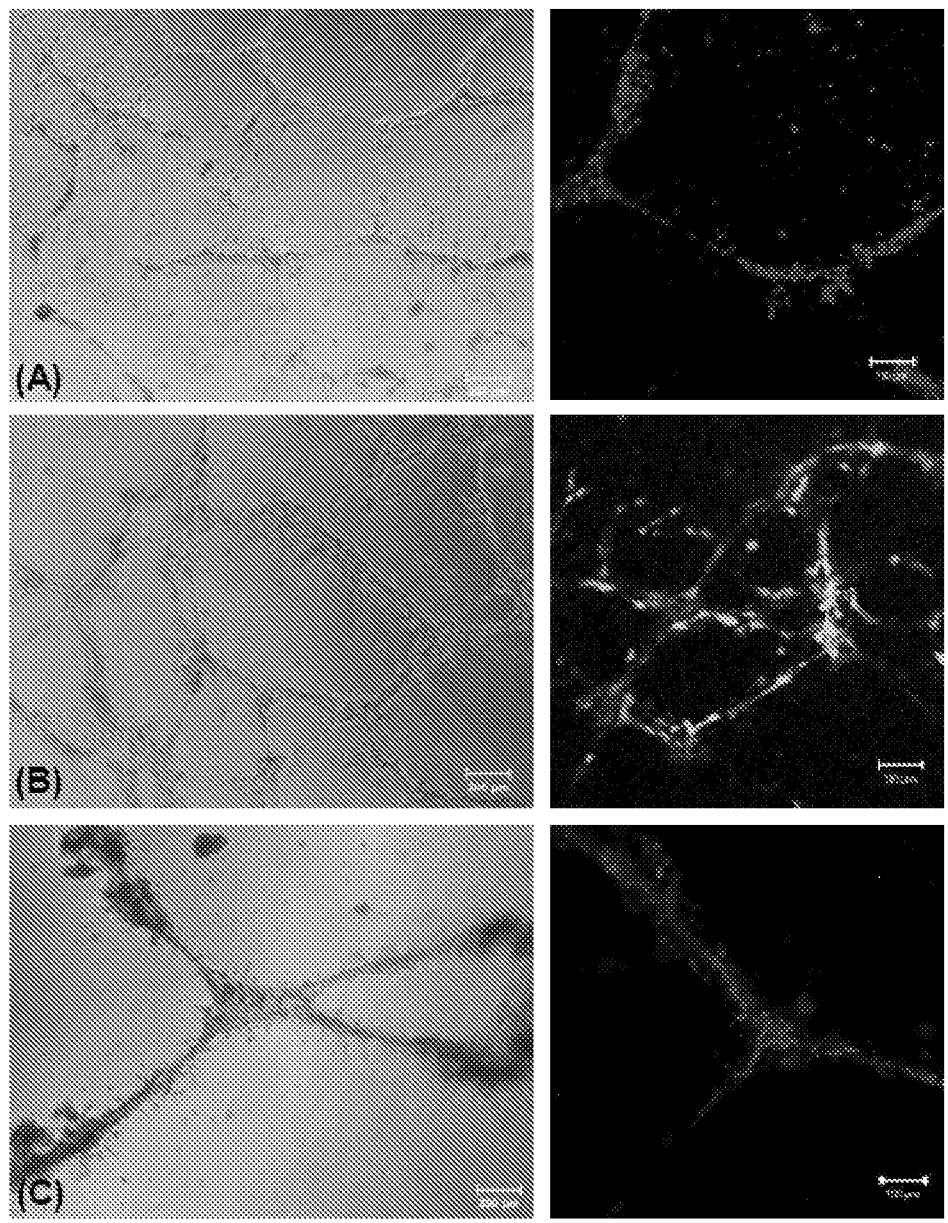
Figure 9(A),(B),(C)

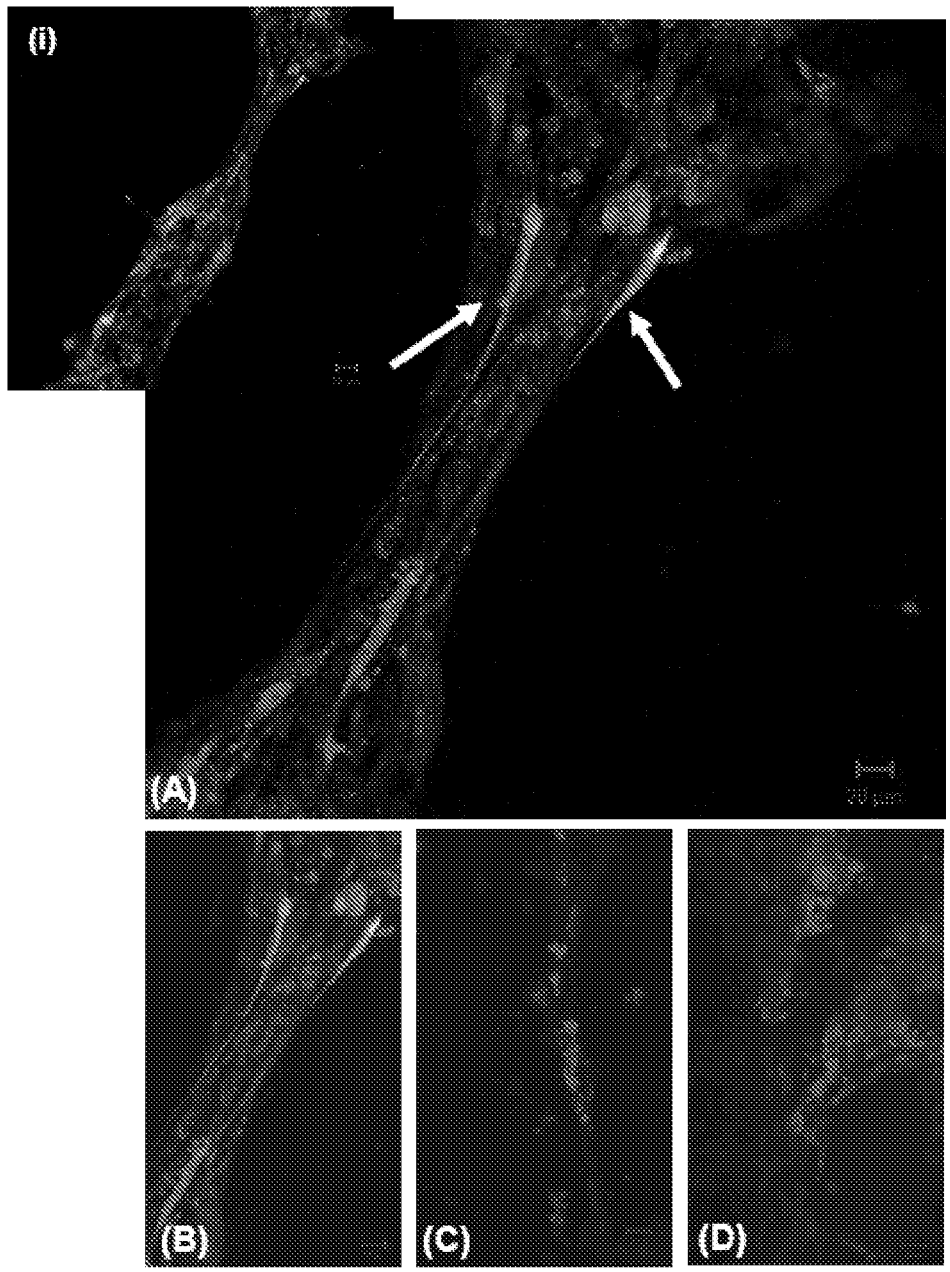
Figure 10(A),(B),(C),(D)

MESENCHYMAL STEM CELL FOR PROMOTING NEOVASCULARISATION

FIELD OF THE INVENTION

The present invention relates to genetically modified mesenchymal stem cells (MSCs), and their use as potential therapeutic agents in tissue regeneration and repair. In particular, the MSCs are genetically modified to express a protein capable of promoting neovascularisation.

BACKGROUND OF THE INVENTION

Non-haematopoietic stem cells obtained from bone marrow called mesenchymal stem cells (MSCs) hold great therapeutic potential in regenerative medicine and tissue engineering owing to their ability to differentiate into osteogenic, adipogenic, chondrogenic, myogenic and possibly neurogenic lineages.[1,2,3] US patent publication numbers 2005/0249731, 2005/0019911 and 2003/0157078 disclose methods of isolating mesenchymal stem cells and the potential use of such cells for tissue repair.

The treatment of cardiovascular disease (CVD) represents one of the many possible target therapeutic applications of MSCs. CVD is the leading cause of death is purported to be responsible for more than 50% of all deaths in Europe. Furthermore, it is estimated that 1 in 4 US residents has CVD in one form or another. Expenditure on the treatment of CVD is estimated to be $393.5 billion (2005) in the US alone, and such figures are expected to grow as the population in Europe and the US ages. Among CVD disorders, ischemic heart disease has emerged as the primary cause of deaths worldwide.

Restoration of a vascular supply to the ischemic heart is of high clinical relevance and pro-angiogenic therapies aim to reduce morbidity and mortality rates associated with the onset of cardiovascular disease. Over the past decade there has been a huge leap in unravelling the molecular mechanisms that govern new blood vessel formation. A number of regulatory factors have been identified as key role players in the formation of blood vessels including the vascular endothelial growth factor (VEGF), platelet derived growth factor (PDGF), and fibroblast growth factor (FGF) families. This new knowledge has allowed the design and implementation of novel pro-angiogenic interventions and therapeutic approaches including gene therapy, cellular therapy and combinations of both.

Adult stem cell therapy holds great promise for cardiac repair by means of regeneration of the myocardium and neovascularisation in arterial occlusive disease. There is increasing evidence that MSCs, derived from bone marrow, can successfully be used to restore cardiac function following ischemic injury. Enhancing the ability of MSCs to promote neovascularisation in the ischemic heart could have an impact in reducing the mortality rates associated with the onset and development of cardiovascular disease.

Stem cell mediated neovascularisation has been heightened by the modification of these cells to over express angiogenic cytokines.[4] Like the development steps in pro-angiogenic gene therapy, initial studies focussed on the over-expression of a single angiogenic factor. VEGF has proved popular, along with other factors such as Ang-1 and HGF, and initial pre-clinical reports point to improvements in myocardial reperfusion over cell therapy alone.[5] Further studies have ultilised a multimodal approach, where a number of factors are over expressed together in MSCs resulting in further increases in global heart function.[6]

Notwithstanding the state of the art it would be still be desirable to provide for alternative MSCs genetically modified to express or over-express a particular protein capable of promoting neovascularisation.

OBJECT OF THE INVENTION

It is an object of the present application to provide an MSC that increases the cell's ability to differentiate along the endothelial lineage. A further object is to provide a treatment for ischemic tissue disorders, cardiovascular diseases, wounds and combinations thereof Ephrin-B2 is a candidate gene that has the potential to increase MSCs' inherent pro-angiogenic capability. The present application describes how cells over-expressing Ephrin-B2 can differentiate along the endothelial cell lineage and the potential of these cells as a new cell source to promote new blood vessel formation.

A further object of the invention is to provide compositions and methods for the promotion of neovascularisation.

SUMMARY OF THE INVENTION

According to the present invention there is provided an isolated mesenchymal stem cell selected from the group consisting of an isolated mesenchymal stem cell that expresses Ephrin-B2, an isolated mesenchymal stem cell that over-expresses Ephrin-B2, and an isolated mesenchymal stem cell that is genetically modified to increase Ephrin-B2 expression. Desirably, the isolated mesenchymal stem cell comprises an isolated mesenchymal stem cell that is genetically modified to increase Ephrin-B2 expression. Over-expression of Ephrin-B2 by MSCs can be achieved in a variety of ways known to the person skilled in the art, for example by viral or non-viral means, such as delivering a polynucleotide to the cell with a liposome or a vector encoding for Ephrin-B2. Some suitable methods are discussed in the Experimental Data section below.

In a further embodiment the invention provides for a pharmaceutical composition comprising a material selected from the group consisting of an isolated mesenchymal stem cell according to the present invention, Ephrin-B2 and combinations thereof together with a pharmaceutically acceptable carrier or excipients. Preferably, the pharmaceutical composition comprises an isolated mesenchymal stem cell according to the present invention together with a pharmaceutically acceptable carrier or excipients. The composition may comprise carriers and excipients, as would be well known to someone of skill in the art. Such compositions may find use in the promotion of neovascularisation. Furthermore, such compositions find use in the treatment of ischemic tissue disorders, cardiovascular diseases such as pulmonary hypertension, wound healing and combinations thereof. As used herein, the term ischemic tissue disorders includes disorders and complications selected from the group consisting of cardiovascular ischemic disorders including myocardial infarction and lower limb ishcemia, mesenteric ischemic disorders, renovascular ischemic disorders and combinations thereof.

The invention also provides for the use of a material selected from the group consisting of Ephrin-B2, a gene encoding Ephrin-B2, a mutant thereof also encoding functional-Ephrin-B2 and combinations thereof in the preparation of a medicament for the promotion of neovascularisation. As will be appreciated by a person skilled in the art, the use of Ephrin-B2 may be selected from the group consisting of a recombinant Ephrin-B2 protein, genetically modified cells such as MSCs to express or over-express Ephrin-B2, and combinations thereof. Desirably, a gene encoding Ephrin-B2 may be utilised in the preparation of a medicament for the promotion of neovascularisation.

The invention further extends to a method of treating ischemic tissue disorders, cardiovascular diseases such as pulmonary hypertension, wounds and combinations thereof, wherein the method of treatment is selected from the group consisting of administering to a patient a pharmaceutically effective amount of Ephrin-B2, administering to a patient a pharmaceutically effective amount of a polynucleotide encoding Ephrin-B2, administering to a patient a pharmaceutically effective amount of an isolated mesenchymal stem cell according to the present invention and combinations thereof. The polynucleotide encoding Ephrin-B2 may be administered as part of a gene therapy technique. Preferably, the method of treatment according to the present invention may comprise administering to a patient a pharmaceutically effective amount of an isolated mesenchymal stem cell according to the present invention.

Co-administration of isolated MSCs according to the present invention and Ephrin-B2 may also be used in these methods. Delivery to the patient may be through the vasculature using an implanted device, intramuscular delivery, intravascular delivery and combinations thereof. The ischemic tissue disorder may be selected from the group consisting of cardiovascular ischemic disorders including myocardial infarction and lower limb ishcemia, mesenteric ischemic disorders, renovascular ischemic disorders and combinations thereof.

The invention provides for a method for identifying compounds for the promotion of neovascularisation comprising contacting a test compound with cells in which Ephrin-B2 expression is down-regulated and determining the effect of the candidate compound on the expression of Ephrin-B2. Ephrin-B2 expression can be measured for example using quantitative real-time PCR or ELISA. Compounds useful in the promotion of neovascularisation may find use in the preparation of medicaments for the treatment of ischemic tissue disorders, cardiovascular diseases such as pulmonary hypertension, wound healing and combinations thereof. The ischemic tissue disorder may be selected from the group consisting of cardiovascular ischemic disorders including myocardial infarction and lower limb ishcemia, mesenteric ischemic disorders, renovascular ischemic disorders and combinations thereof.

In a further embodiment the invention extends to a medical device coated with an isolated mesenchymal stem cell according to the present invention. The medical device may be selected from the group consisting of a stent, a suture, a bandage, a dressing, a prosthesis, biomaterials engineered for wound healing and combinations thereof.

The invention further provides for the use of a material selected from the group consisting of a gene encoding Ephrin-B2, a mutant thereof also encoding functional-Ephrin-B2, an isolated mesenchymal stem cell according to the present invention and combinations thereof in tissue engineering. As used herein tissue engineering may comprise the preparation of vascular bypass grafts, vascularised tissue constructs and combinations thereof. Suitable constructs may comprise bone, muscle, liver, etc. Such examples are by no means limiting and it should be readily apparent to one of ordinary skill in the art that other constructs are possible and embraced by the present invention. Desirably, an isolated mesenchymal stem cell according to the present invention may be utilised in tissue engineering.

BRIEF DESCRIPTION OF THE DRAWINGS

Additional features and advantages of the present invention are described in, and will be apparent from, the detailed description of the invention and from the drawings in which:

FIGS. 1A-1D illustrate MSC characterisation and differentiation potential.

FIGS. 2A-2H depict the amplification of the full coding sequence of Ephrin-B2 and subsequent TA cloning into the pTargeT mammalian expression vector according to the present invention. This was a three way process, amplification of the coding sequence, TA cloning in pTargeT and then subcloning of the coding sequence into pIRES2-eGFP. This was the vector that all subsequent experiments were carried out on.

FIGS. 3A-3E display the results of Nucleofection of MSCs with pIRES2-eGFP/Ephrin-B2 according to the present invention.

FIGS. 5A-5C show the osteogenic potential of Ephrin-B2 over-expressing MSCs.

FIGS. 6A-6E portray the effect of Ephrin-B2 over-expression on MSC tubule formation.

FIGS. 9A-9C display co-cultures of MSCs/Ephrin-B2 with Endothelial cells in the assessment of tubule formation.

FIGS. 10A-10D illustrates the structural organisation of EC-MSC/Ephrin-B2 co-cultured tubules relative to control MSCs.

DETAILED DESCRIPTION OF THE INVENTION

Figure 2B:
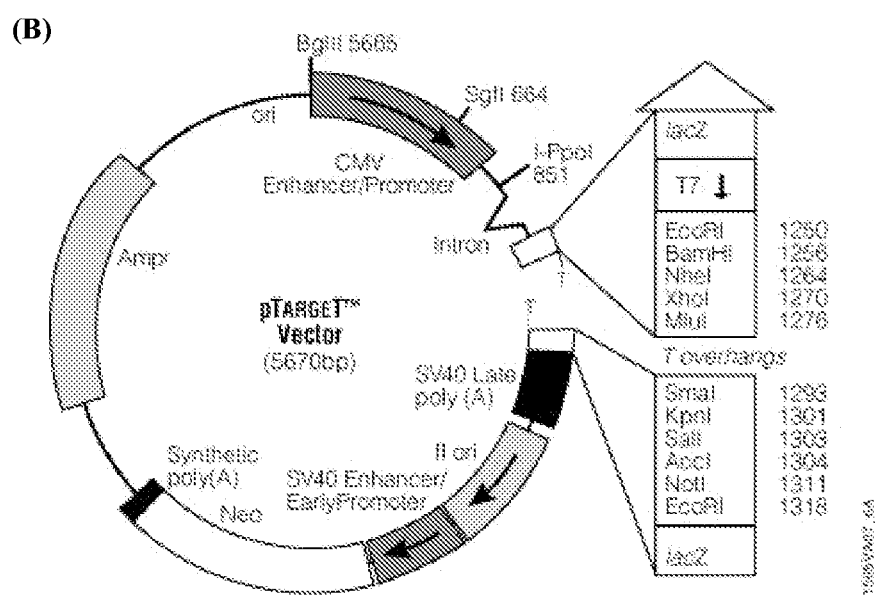

The Eph (erythropoietin-producing hepatocellular carcinoma) receptors and their cell surface anchored ligands, the Ephrins, comprise the largest of the receptor tyrosine kinases families with 14 receptors and 8 ligands. The receptors are subdivided into Eph-A and Eph-B categories based on sequence homologies and binding properties to Ephrin ligands and have known actions in the development of the vascular and nervous system. Eph-A receptors bind to GPI-anchored Ephrin-A ligands whereas Eph-B receptors bind to Ephrin-B ligands that contain transmembrane and cytoplasmic domains. Eph receptor tyrosine kinases and their Ephrin ligands regulate a diverse array of cellular functions including cell migration, repulsion and adhesion and somite formation. These functions are dependent on cell-cell contact which initiates bidirectional signalling between cells expressing the receptors (forward signalling) and cells expressing the ligands (reverse signalling). Eph-B4 and Ephrin-B2 are co-expressed in the yolk sac, the first site of hematopoiesis and vascular development during embryogenesis. Ephrin-B2 is specifically expressed in arterial angioblasts and endothelial and perivascular mesenchymal cells, whereas Eph-B4 is expressed on ECs belonging to the venous lineage.

Experimental Data
Materials and Methods
Mesenchymal Stem Cell Isolation and Expansion Bone marrow aspirates were obtained from the iliac crest of normal donors; all procedures were performed with informed consent and approved by the Clinical Research Ethical Committee at University College Hospital, Galway. Mesenchymal Stem Cells were isolated and expanded in culture as described previously by direct plating.[7] Briefly, aspirates were washed with medium [DMEM-low glucose containing 1% antibiotic] and centrifuged; the precipitated cells were suspended in medium with 10% selected fetal bovine serum and plated at a final density of approximately $3.0 \times 10^5$ cells/cm$^2$. Cells were seeded on T-175 flasks and maintained at 37° C. with 95% humidity and 5% $CO_2$ in the same medium. After 5 days red blood cells were washed off with phosphate-buffered saline and fresh medium added. Colonies of adherent cells formed within 9 days. At the end of primary culture, adherent colonies were detached by treatment with 0.25% trypsin and 0.53 mM EDTA. Cells were plated in medium [DMEM-LG; 10% FBS; 1% antibiotic (all from Sigma Aldrich)] at $5.7 \times 10^3$ cells/cm$^2$. Cultures were passaged at 4-6 day intervals and expanded to passage 5 for experimentation.

Osteogenic Differentiation Assays

To assess the osteogenic potential of MSCs, cells were plated at 30,000 cells per well of a 6 well plate and cultured overnight. The following day cells were treated with osteogenic media [DMEM low glucose; 100 nM dexamethasone; 10 mM β-glycerophosphate; 50 µM ascorbic acid 2-phosphate; 10% FB; 1% antibiotic (Sigma-Aldrich)]. Media was replaced 2 times per week. The plates were assayed for calcium deposition on day 15. Wells were fixed with 10% neutral buffered formalin for 10 minutes and washed with deionised water. 1 ml of 3% silver nitrate solution was added to each well and incubated at room temperature in the dark for 10 minutes. Wells were rinsed and exposed to bright light for 15 minutes and calcium deposits imaged. Cells grown in regular MSC media acted as controls. Quantification of mineral deposition was performed as previously described;[8] briefly wells were washed with water and 1.5 mL of 1N HCl was added to each well and the contents of the well scraped into a 1.5 mL eppendorf tube. After shaking overnight at 4° C., the calcium concentration was quantified using a colometric calcium assay versus a standard curve (Calcium (CPC) Liquicolour; Stanbio Inc.).

Fc-Chimera Protein Binding Assay

Cells were detached from the flask using cell dissociation agent (MP Bio) washed in D-PBS (−)/5% FBS twice and incubated with 2 µg/mL Fc-chimera proteins (Ephrin-B2, Eph-B4 or CD6/Fc) for 30 minutes on ice. After a further two washes cells were incubated with FITC-conjugated goat anti-human IgG1 antibody for 30 minutes at room temperature. After a further two washes stained cells were analysed using the GUAVA EasyCyte or the BD LSR. Histograms of cell number versus fluorescence intensity were recorded for 10,000 cells per sample and analysed using FCS Express 2 (DeNovo Software).

Western Blotting

Cell protein lysates from hMSCs were separated on 10% SDS-polyacrylamide gels (Novex) and transferred onto PVDF membranes (Milipore). Immunoblotting was performed with a rabbit polyclonal anti-Ephrin-B2 primary antibody (Santa Cruz) and detected using a goat anti-rabbit horseradish peroxidase conjugated secondary antibody (Abcam). Immunoreactive proteins were visualised with the enhanced chemiluminesence kit (Amersham). CD29 (Integrin β1) acted as a positive MSC marker control.

Cloning of an Ephrin-B2 Mammalian Expression Vector

The full length coding sequence of Ephrin B2 was amplified from human coronary artery endothelial cell mRNA using two step RT-PCR carried out with a proof reading taq (PFX) that added a poly-a tail at both 5' and 3' ends. Coding primer sequences—

```
                                          (SEQ ID NO. 1)
    forward     (5'ATGGCTGTGAGAAGGGACTCC), (SEQ ID NO. 2)
    reverse     (5' TCAGACCTTGTAGTAAATGTTC).
```

Following amplification, the cloning sequence was initially cloned into the TA- pTargeT Expression Vector (Promega) in a sterile 0.5ml eppendorf tube. Inserts were verified with DNA sequencing (MWG Biotech—Genome Sequencing Services). Subsequently Ephrin B2 was subcloned from the pTargeT vector to the pIRES2-eGFP bicistronic mammalian expression vector (Clontech). Insertion was verified by restriction endonuclease mapping and 11 positive clones were found. All experiments were carried out with Clone 11A (pEphrin-B2/IRES-eGFP) and expression of Ephrin B2 was confirmed in HEK 293 cells by transient transfection and immunoblotting.

Nucleofection & Transgene Analysis

MSCs at passage 5 were washed with hanks balance salt solution (Sigma) and harvested by trypsinisation. Cells were counted and $5\times10^5$ cells were resuspended in 100 µl of pre-warmed Human MSC Nucleofection Solution (Amaxa). 2 µg of plasmid DNA in TE buffer (pmaxGFP, pIRES2-eGFP, pIRES2-eGFPEphrin B2) was added to the cell suspension. The sample was transferred into an Amaxa cuvette and placed into the holder of the Nucleofector Device II (Amaxa Biosystems) and subjected to the high transfection efficiency program (U-23). The cuvette was removed immediately and 500 µl of pre-warmed growth media was added to the cell suspension and transferred to a T25 cell culture flask. The cells were incubated in a humidified 37° C./5% CO2 incubator for 24 hours. After 8 hours of culture, viability was assessed by the proportion of cells attached to the culture surface using a coulter counter. Cell viability was also measured by trypan blue exclusion. pmaxGFP acted as a positive nucleofection control and cells minus DNA acted as a negative control. GFP/eGFP Transgene expression was analysed 24 hours after nucleofection by flow cytometry. The percent of GFP/eGFP positive cells were quantified versus negative control over 10 days using the BD LSR and analysed using FCS Express 2 (DeNovo Software). Western blot analysis and Eph-B4/Fc binding assays were carried out as described previously to verify the increased expression of Ephrin-B2 in transfected MSCs.

Matrigel Assay—Vessel Formation Assay

Growth factor reduced Matrigel (120 ul; BD Biosciences) was placed in each well of an ice-cold 48-well plate. The plate was placed at 37° C. for 30 minutes to permit Matrigel to solidify. To assess the effect of over-expression of Ephrin-B2 on MSC tubule formation, cells were detached 48 hours after nucleofection and plated at $3\times10^4$ cells per well. Furthermore to assess the effect of transfected MSCs on endothelial cell tubule formation ECs were detached, labeled with 2 µM PK26 (Sigma Aldrich) and plated at $3\times10^4$ cells per well. MSCs were added to EC's at a ratio of 1:2 24 hours after EC seeding. MSC and EC/MSC tube formation was visualized periodically over 72 hours and at 5 days of co-culture. Phase images were acquired using a Zeiss Axiovert 200 microscope and Spot v4.6 digital imaging system. Confocal images and z stacks were taking with a Zeiss LSM 510 and LSM Image Examiner.

MSC/Ephrin-B2—Endothelial Cell Differentiation and Phenotype Analysis

T25 cell culture flasks were coated with a thin layer of growth factor reduced Matrigel (150 µg/mL) for 2 hours. MSCs, MSCs/eGFP and MSC/Ephrin B2 were seeded on the matrigel coated flasks and cultured in EGM-2 growth media for 5 days. Phase images were acquired using a Zeiss Axiovert 200 microscope and Spot v4.6 digital imaging system. Cells were harvested and fixed for 15 minutes in 4% paraformaldehyde. Cells were washed in PBS (−)/5% FBS and permeabilised with 0.1% triton X 100/PBS for 5 minutes. Cells were incubated with one of the following antibodies: anti-SMC (goat anti-human; Sigma), anti-vWF-PE (Dako), anti-Flk-1 (rabbit anti-human; Fitzgerald), and anti-CD73-PE (BD), for 1 hour at room temperature. After washing, cells stained with unconjugated primary antibodies were incubated with alexa fluor 546 conjugated anti-goat/rabbit secondary antibodies (Molecular Probes) for 1 hour at room temperature. Histograms of cell number versus fluorescence intensity were recorded for 10,000 cells per sample at each time point with the BD LSR and analysed using FCS Express 2 (DeNovo Software).

Assay for VEGF Production

After a 5 day exposure of MSCs/Ephrin-B2 to endothelial conditions, $5\times10^5$.MSCs were seeded in 6 well plates in serum free media. The cells were placed in a hypoxic chamber at 0.1% O2 for 4 hours. Conditioned media was collected and the amount of VEGF produced was measured using a Quantikine human VEGF immunoassay kit (RnD Systems). Non-modified cells acted as controls.

Statistical Analysis

All values are presented as the mean±standard deviation of the mean (SD). Datasets were tested for significance using the student's t-test or a general linear model two-way ANOVA in combination with a post hoc Tukey test to compare between groups. A level of p<0.05 was considered statistically significant.

Results

MSCs were Isolated from the Bone Marrow and Expressed Characteristic Cell Surface Markers.

Cell isolation, expansion and differentiation of MSCs using direct plating was established according to other reports.[7] Isolated MSCs adhered to culture plastic had a fibroblastic morphology as shown by the phase contrast micrograph in FIG. 1A, and proliferated up to passage five with a doubling time of approximately 2 days. Flow cytometry histograms indicate the fluorescent intensity of unstained cells (solid), or cells labeled with anti-CD45, -CD73, -CD105 antibodies, or-mouse IgG 1 isotype control, as shown in FIG. 1B. The isolated cells were negative for CD45, a known hematopoietic marker, but positive for MSC characteristic markers CD73 and CD105. MSCs cultured in adipogenic and osteogenic differentiation conditions for 15 days stained positively with Oil red O for lipid droplets in the cytoplasm (FIG. 1C) and Von Kossa for calcium deposits in the well as shown in FIG. 1D.

Cloning of Ephrin-B2 into a Bicistronic Mammalian Expression Vector:

To further understand the role of Ephrin-B2 function in MSCs we aimed to clone the full coding sequence of the gene into a mammalian expression vector and over express it in the cells. The initial gateway construct was generated using TA cloning of the Ephrin-B2 amplified PCR product into the pTargeT mammalian expression vector with gene expression under the control of the cytomegalovirus (CMV) promoter. FIG. 2A is an image of a 1% agarose gel showing 1 kb bands of Ephrin-B2 amplified from the mRNA of human coronary artery endothelial cells by PCR. FIG. 2B represents a diagrammatic map of the pTargeT mammalian expression vector and its multiple cloning sites. The Ephrin-B2 PCR products were TA cloned into the pTarget Vector.

Figure 2D:
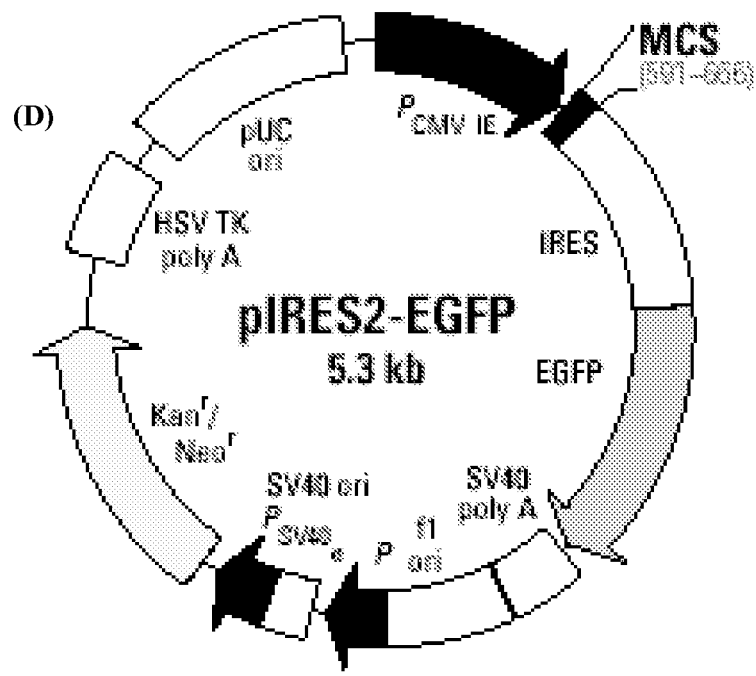

Three positive clones with Ephrin-B2 inserted were verified by restriction enzyme digestion with SalI and BamHI after blue white screening. FIG. 2C provides an image of a 1% agarose gel illustrating three successful clones derived from blue white screening (2a21, 2c21 and 2g21) after the insertion of Ephrin-B2 into the pTargeT vector. The positive clones with inserted Ephrin-B2 were linearised (left lane) with MluI restriction enzyme digestion or double digested (right lane) with MluI and BamHI. A band corresponding to the insert Ephrin-B2 (1041 kb) can be clearly seen in each positive clone (arrow). The complete and correct gene sequence was also verified by gene sequencing. Subsequently, Ephrin-B2 was sub-cloned from the pTargeT vector into pIRES2-eGFP mammalian expression vector. A diagrammatic map of the pIRES2-eGFP bicistronic mammalian expression vector is shown in FIG. 2D. FIG. 2Ei depicts a 1% agarose gel image of pIRES2-eGFP digested with BamHI and SalI restriction enzymes resulting in a 6 kb linearised DNA band. Similarly, FIG. 2Eii is a gel image of pTargeT/Ephrin-B2 positive vector digested with BamHI and SalI, a 1 kb band can be seen corresponding to the Ephrin-B2 product. The correct insertion and orientation of the Ephrin-B2 gene was analysed by restriction enzyme mapping. A gel image showing the banding pattern of the correct orientation of the insert restriction digested with SalI and XbaI is given in FIG. 2H. 3 Partial bands are visible at 369, 1992 and 4009 kb respectfully. A total of 11 clones with Ephrin-B2 inserted correctly into the pIRES2-eGFP backbone were found. All experiments were carried out using clone 100A (arrow).

Figure 3B:
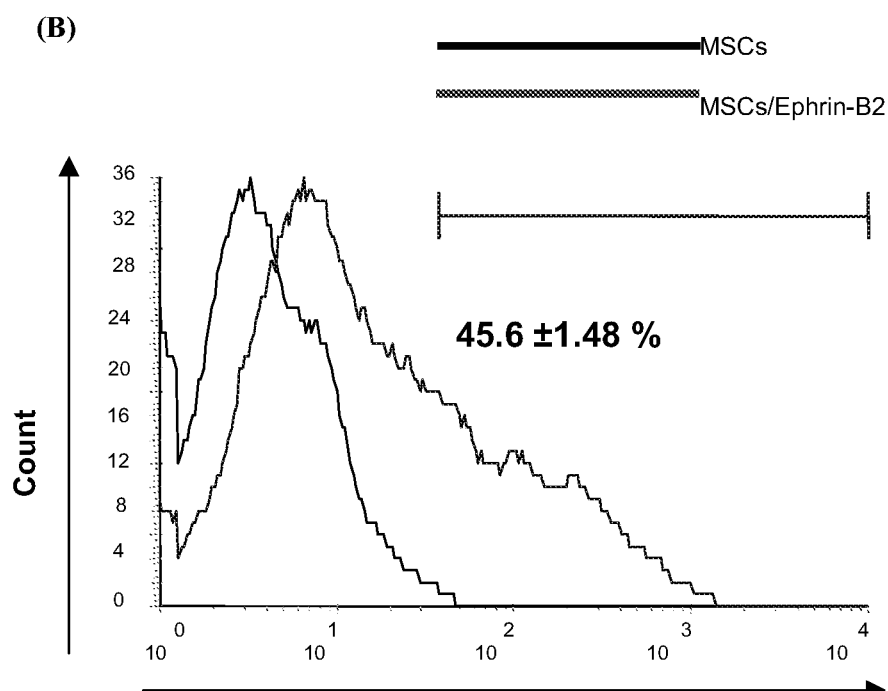
Figure 3E:
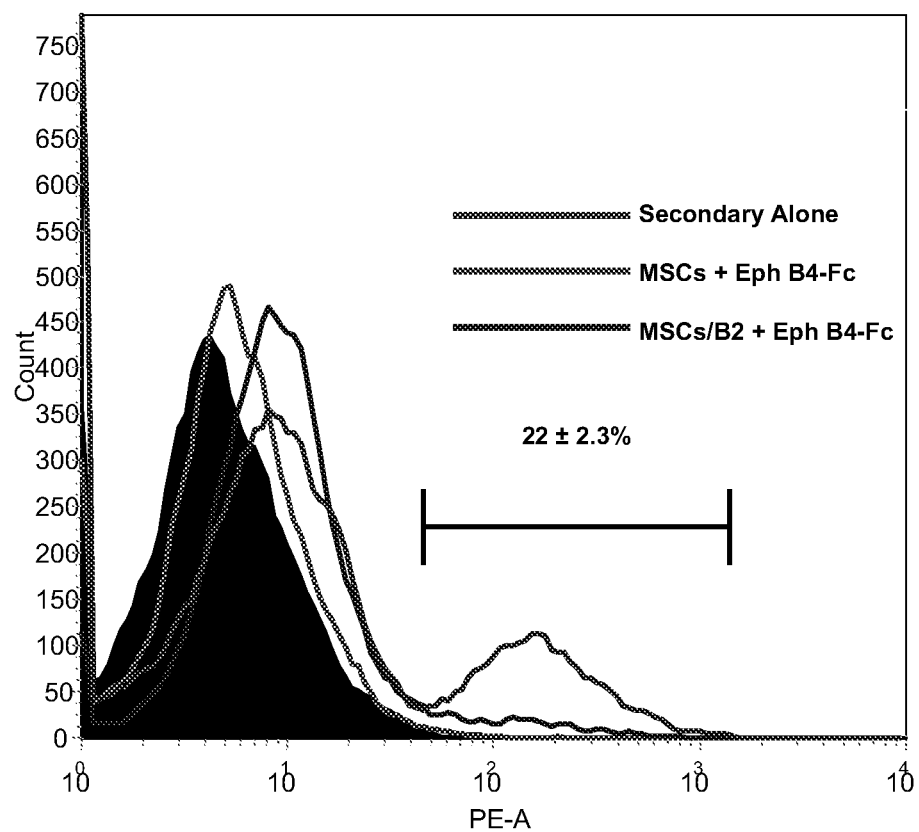
Figure 4:
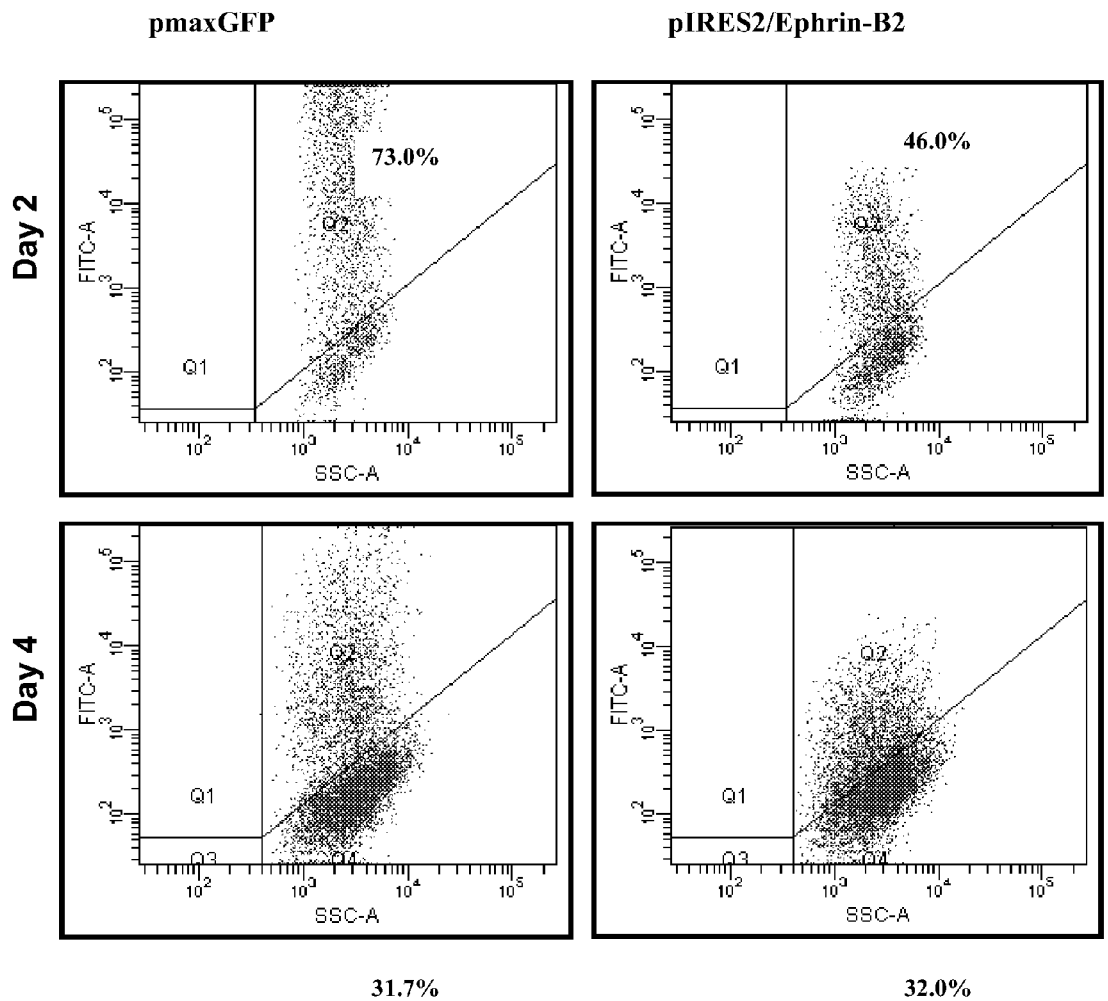
FIG. 4 illustrates that the expression of Ephrin-B2/eGFP in MSCs is transient.
Figure 4:
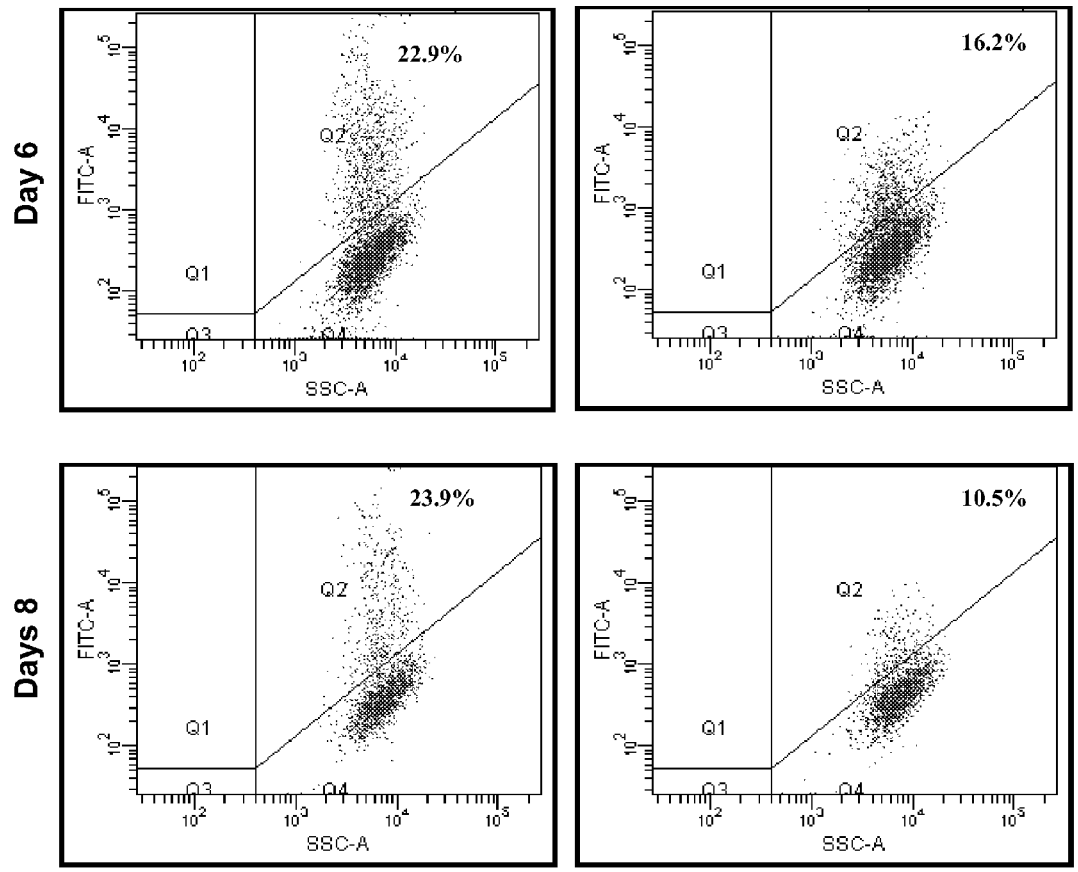
Figure 4:
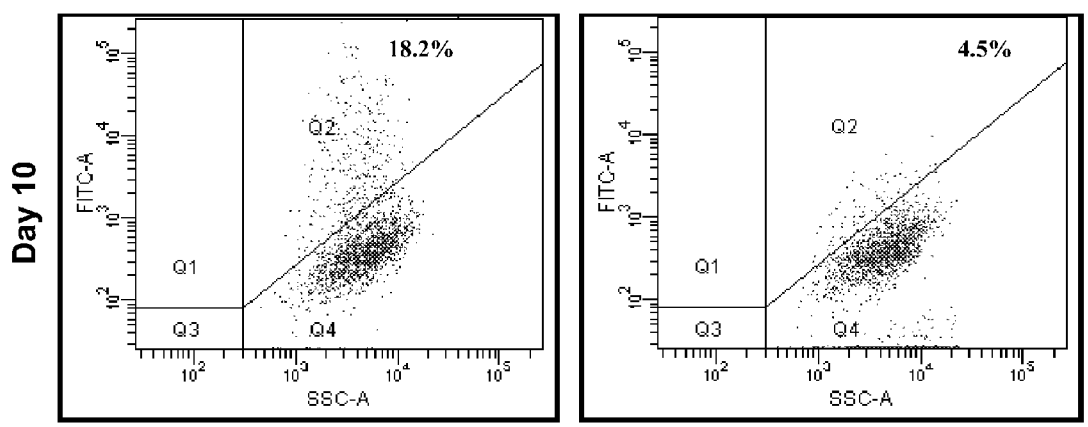

Nucleofection of MSCs with pIRES2-eGFP/Ephrin-B2:

MSCs were transfected with the pEphrin-B2/eGFP plasmid using a nucleofection technique previously described.[9,10] Transfection efficiency was measured by analysing the expression of eGFP in cells using both microscopy and FACS analysis. A transfection efficiency of 45.6±1.48% was achieved with the pEphrin-B2/eGFP vector, while viability was reduced to 66.3±1.48% after nucleofection. FIG. 3A is a quantitative analysis of GFP/eGFP expression in MSCs nucleofected with pEphrin-B2/IRES2-eGFP using amaxa hMSCs reagent, cell transfected with pmaxGFP acted as a nucleofection control. FIG. 3B portrays a flow cytometry histogram showing the level of GFP expression of MSCs transfected with pEphrin-B2/IRES2-eGFP. GFP positive cells were clearly seen in fluorescent micrographs 48 hours after transfection as shown by the arrows in FIG. 3C. Cells remained viable in culture and expanded over 6 days (data not shown). To assess the transient nature of transfection we analysed the percentage of eGFP positive cells every 2 days over 10 days in culture. There was a marked drop of expression from 46.8% to 4.5% over the time period as illustrated in the right-hand panel of the flow cytometry scatter plots of GFP/eGFP positive cells shown in FIG. 4. The pmaxGFP vector acted as a positive transfection control, and also showed a decrease in GFP expression from 73% to 18.2% over the same 10 day period, shown in the left-hand panel of FIG. 4. We next examined the expression of the transgene, Ephrin-B2, 48 hours after transfection by western blotting and the binding of its cognate receptor, Eph-B4/Fc. A Western blot showing Ephrin-B2 protein expression in MSCs 48 hours after transfection with p Ephrin-B2/IRES2-eGFP is given in FIG. 3D. Untransfected MSCs—lane 1, Transfected MSCs—lane 2. β-actin acted as a loading control. Cells increased expression of Ephrin-B2 as seen with the increase in expression in lane 2 versus MSCs alone. FIG. 3E is a flow cytometry histogram showing the binding of pre-clustered Eph-B4/Fc protein to transfected and normal MSCs. There is an increase in the expression of Ephrin-B2 on the cell surface of nucleofected cells. There was also an increase in the binding of Eph B4/Fc to the cell surface of transfected MSCs by 22±2.3% compared to normal cells.

MSCs Over-Expressing Ephrin-B2 Lose Their Osteogenic Differentiation Potential

To assess changes in the differentiation potential of MSCs/Ephrin-B2, osteogenic induction was initiated 48 hours after nucleofection. From the representative phase micrographs of normal and transfected cells over 15 days of osteogenic differentiation (scale bar indicates 200 μm) in FIG. 5A it is apparent that the cells over expressing Ephrin-B2 adopted a morphology similar to endothelial cells at day 2, 5 and 8 after osteogenic induction when compared to cells alone. At day 15 however, MSCs/Ephrin-B2 appeared similar in morphology to osteogenic MSCs but with a reduced cell number. Transgene expression was returning to normal levels at this time point. FIG. 5B illustrates that there was a significant reduction in the amount of calcium deposited by MSCs/Ephrin-B2 in comparison to normal MSCs at day 15 of osteogenic induction (p<0.01). Data are presented as the mean±SD of calcium concentration (μg) per well, n=3. (*) indicates p<0.05 versus Osteo alone. Light micrographs of Von Kossa stained osteogenic cultures given in FIG. 5C illustrates that there are visibly less stained calcium deposits in transfected cells (200×). Cells in normal media acted as controls. The data collectively indicate that there is a loss in the differentiation potential of MSCs over expressing Ephrin-B2 towards the osteogenic lineage.

Over-Expression of Ephrin-B2 in MSCs Increases Tubule Formation:

To further understand the changes in the cellular phenotype seen after Ephrin-B2 over-expression the tubule formation potential of transfected MSCs was analysed. Two days after transfection cells were plated on growth factor reduced matrigel and tubule formation was imaged 24 hours later. It was immediately apparent that MSCs over expressing Ephrin-B2 (FIG. 6B) had an increased potential to form tubules on the matrigel compared to normal MSCs (FIG. 6A) which formed large cellular aggregates on the gel surface as illustrated in and. Using confocal fluorescent microscopy we subsequently investigated the incorporation of eGFP positive cells into tubules formed on the matrigel as transfected cells express both eGFP and Ephrin-B2 (because of the bi-cistronic expression system). Fluorescent confocal micrographs of MSCs (FIG. 6C) and MSCs/Ephrin-B2 (FIG. 6D) also show large cellular clusters form when MSCs are cultured on matrigel whereas MSCs/Ephrin-B2 form numerous tubule structures. FIG. 6E provides representative phase images of tubules still apparent 5 days after cultures in MSCs/Ephrin-B2; MSCs alone acted as controls as seen with the large number of DAPI stained nuclei in cell bundles.

Figure 7A:
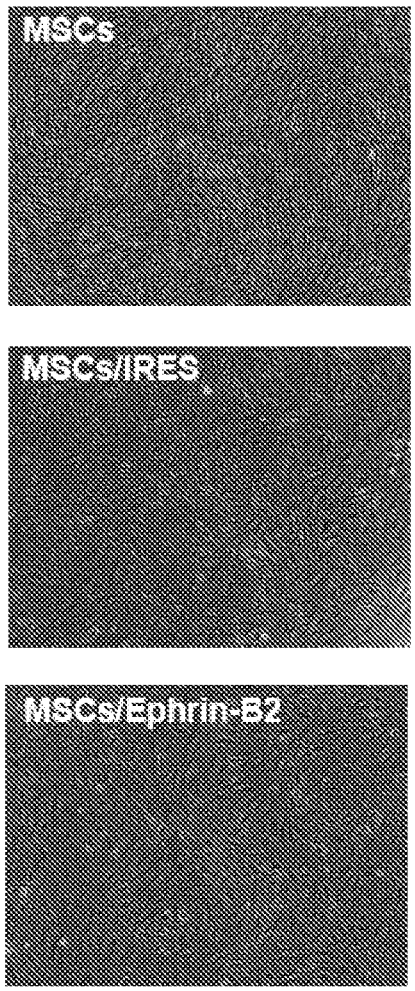
FIGS. 7A-7B illustrate cellular phenotype analysis of MSCs-Ephrin-B2 under endothelial culture conditions.
Figure 7B:
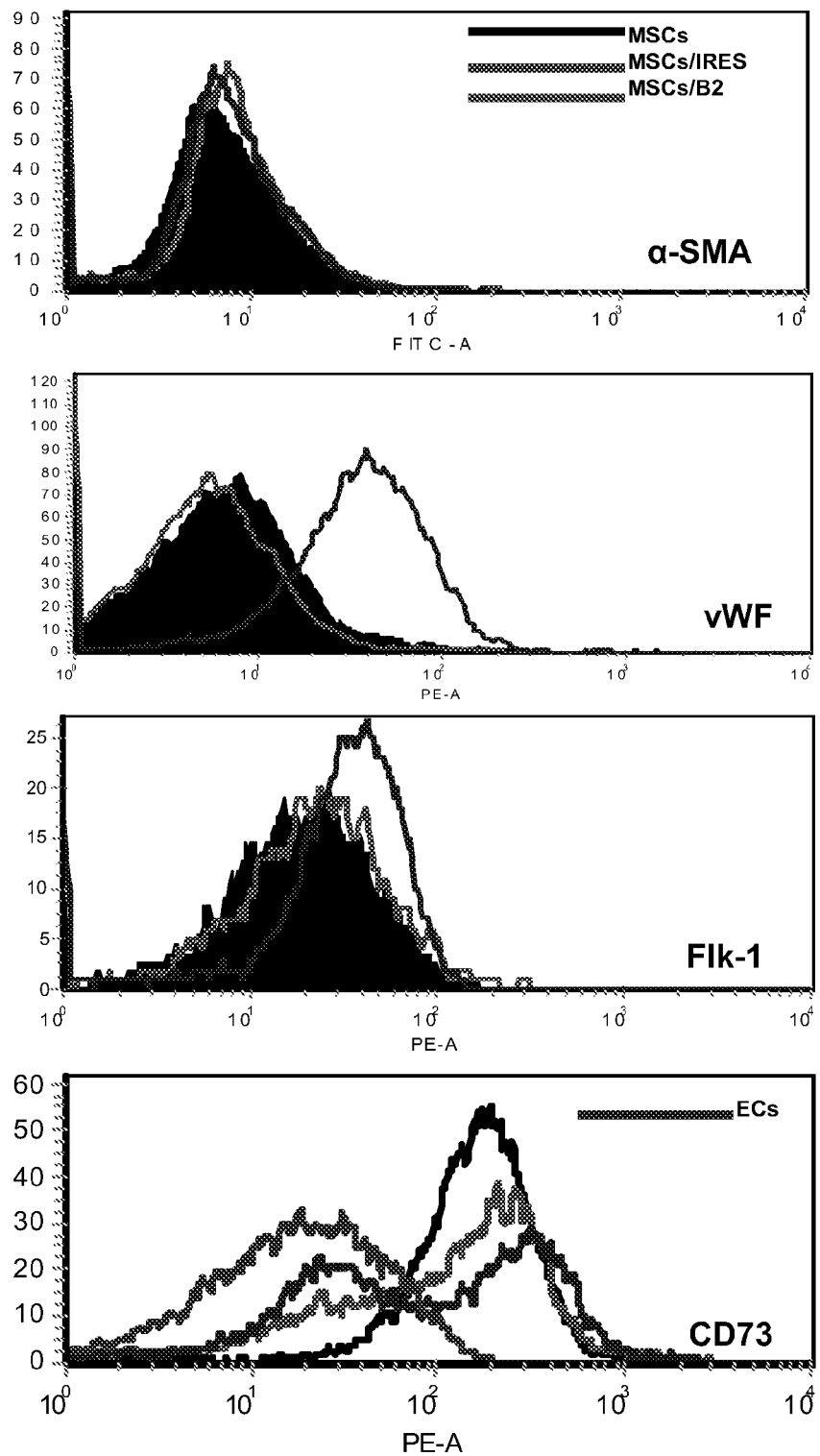
Figure 8:
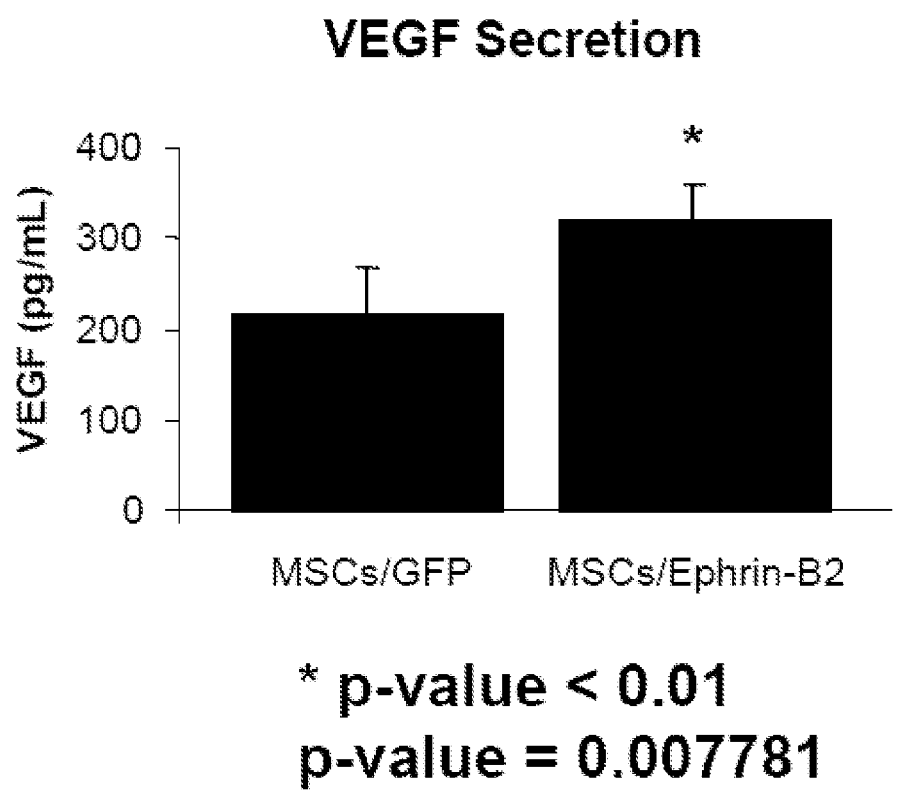
FIG. 8 is a graphical representation showing MSCs/Ephrin-B2 VEGF production under hypoxia.

MSCs/Ephrin-B2 Adopt an Early Endothelial Phenotype Under Endothelial Culture Conditions:

To further characterise the cellular phenotype of the MSCs/Ephrin-B2, MSCs/eGFP and MSCs after 5 days under endothelial cell culture conditions, cells were grown on a thin layer of matrigel in endothelial media for 5 days. The phase micrographs are given in FIG. 7A. The expression of early endothelial markers (VEGF-R1 and Flk-1) were assessed by antibody staining and FACS analysis. The flow cytometry histograms in FIG. 7B show that BMSCs/Ephrin B2 increased the expression of both early endothelial markers, von Willebrand Factor and the VEGF-receptor-1, Flk-1, while there was no appreciable change in expression in MSCs/eGFP or MSCs. Staining for alpha-smooth muscle actin acted as a negative control. Cells did not initially express alpha smooth muscle actin and there were no changes in expression levels after culture. Expression of CD73 was also analysed as an MSC marker control. Interestingly there was a decrease in the expression of CD73 on MSCs/Ephrin-B2 compared to MSCs/eGFP and MSCs after EC culture. On further inspection this reduction corresponded to the level of CD73 normally expressed on aortic endothelial cells. This data suggest that MSCs/Ephrin-B2 adopt an early endothelial phenotype after exposure to EC cell culture conditions. To further characterise the transfected cell population, MSCs/Ephrin-B2 and MSCs/eGFP were cultured under hypoxic conditions for 4 hours and VEGF production was measured. MSCs over expressing Ephrin-B2 released significantly higher levels of the pro-angiogenic factor VEGF compared to MSCs/eGFP. The results are plotted graphically in FIG. 8, which is a quantitative analysis of VEGF production after 5 hours of hypoxia (0.1% $O_2$). Data are presented as the mean±SD of VEGF concentration (pg/mL), n=6. (*) indicates p<0.01 versus MSCs/eGFP.

MSCs/Ephrin-B2 Incorporate with New Tubules Formed by Endothelial Cells:

To assess the ability of MSCs/Ephrin-B2 cells to incorporate into newly formed EC tubules, we co-cultured endothelial cells with MSCs on growth factor reduced matrigel. Representative phase and confocal images of ECs alone, ECs and MSCs/Ephrin-B2, and ECs and MSCs co-cultured on matrigel for 24 hours at a 2-1 ratio, are shown in FIGS. 9A-9C respectively. MSCs were added 24 hours after EC seeding and visualised using phase and multiphoton microscopy. Scale bars indicate 200 μm (phase) and 100 μm (confocal). Endothelial cells were labelled with PKH26 cytoplasmic dye (red). MSCs normally wrap around the EC tubules and form more stable vessel like structures, such as that shown in FIG. 9C. Interestingly after transfection MSCs/Ephrin-B2 incorporated into new EC tubules rather than wrap around the outside layer, which is depicted in FIG. 9B. MSCs over-expressing Ephrin-B2 also express the second cistron transgene (eGFP) and can be seen incorporating into EC tubules. FIGS. 10A-10B illustrate multiphoton fluorescent micrographs of tubules formed during EC co-culture with MSCs/Ephrin B2. eGFP tagged MSCs are visible incorporating into a tubule structure and elongating along the tubule length (arrows) after 72 hours of culture; inset—confocal interference reflection micrograph. FIGS. 10C-10D show ECs and ECs co-cultured with MSCs, which acted as controls. Scale bar indicates 20 μm.

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Throughout this disclosure, various publications, patents and published patent specifications are referenced by an identifying citation, the full bibliographic citation for some of which is found immediately preceding the claims. The disclosures of these publications, patents and published patent specifications are hereby incorporated by reference into the present disclosure to more fully describe the state of the art to which this invention pertains.

REFERENCES

[1] Barry F. P. and Murphy J. M., Mesenchymal stem cells: clinical applications and biological characterization, *Int J Biochem Cell Biol*, 2004, 36(4), 568-584.

[2] Lin J. R., et al., In vitro culture of human bone marrow mesenchymal stem cell colonies and induced differentiation into neuron-like cells. Di Yi Jun Yi Da Xue Xue Bao, 2003, 23(3), 251-3, 264.

[3] Jones, E. A., et al., Isolation and characterization of bone marrow multipotential mesenchymal progenitor cells, *Arthritis Rheum*, 2002. 46, 12, 3349-3360.

[4] Dzau V. J., Gnecchi M. and Pachori A. S., Enhancing stem cell therapy through genetic modification, *J Am Coll Cardiol*, 2005, 46, 1351-1353.

[5] Yang J., Zhou W., Zheng W., Ma Y., Lin L., Tang T., Liu J., Yu J., Zhou X. and Hu J., Effects of myocardial transplantation of marrow mesenchymal stem cells transfected with vascular endothelial growth factor for the improvement of heart function and angiogenesis after myocardial infarction, *Cardiology*, 2007, 107, 17-29.

[6] Yau T. M., Kim C., Li G., Zhang Y., Fazel S., Spiegelstein D., Weisel R. D. and Li R. K., Enhanced angiogenesis with multimodal cell-based gene therapy, *Ann Thorac Surg*, 2007, 83, 1110-1119.

[7] Murphy J. M., Fink D. J., Hunziker E. B. and Barry F. P., Stem cell therapy in a caprine model of osteoarthritis, *Arthritis Rheum*, 2003, 48, 3464-3474.

[8] Jaiswal N., Haynesworth S. E., Caplan A. I. and Bruder S. P, Osteogenic differentiation of purified, culture-expanded human mesenchymal stem cells in vitro, *J Cell Biochem*, 1997, 64, 295-312.

[9] Aslan H., Zilberman Y., Arbeli V., Sheyn D., Matan Y., Libergall M., Li J. Z., Helm G. A., Gazit D. and Gazit Z., Nucleofection-based ex vivo nonviral gene delivery to human stem cells as a platform for tissue regeneration, *Tissue Eng*, 2007, 12, 877-889.

[10] Haleem-Smith H., Derfoul A., Okafor C., Tuli R., Olsen D., Hall D. J. and Tuan R. S., Optimization of high-efficiency transfection of adult human mesenchymal stem cells in vitro, *Mol Biotechnol*, 2005, 30, 9-20.

The invention claimed is:

1. An isolated CD45-negative mesenchymal stem cell that is genetically modified to increase Ephrin-B2 expression.

2. A pharmaceutical composition comprising an isolated mesenchymal stem cell as claimed in claim 1 and Ephrin-B2 and a pharmaceutically acceptable carrier or an excipient.

3. A pharmaceutical composition comprising an isolated mesenchymal stem cell as claimed in claim 1 and a pharmaceutically acceptable carrier or an excipient.

4. A medical device coated with an isolated mesenchymal stem cell according to claim 1.

5. A medical device according to claim 4 wherein the medical device is selected from the group consisting of a stent, a suture, a bandage, a dressing, a prosthesis, biomaterials engineered for wound healing and combinations thereof.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: Forward Primer

<400> SEQUENCE: 1
atggctgtga gaagggactc c                           21

<210> SEQ ID NO 2
<211> LENGTH: 22
<212> TYPE: DNA
<213> ORGANISM: Artificial
<220> FEATURE:
<223> OTHER INFORMATION: Reverse Primer

<400> SEQUENCE: 2
tcagaccttg tagtaaatgt tc                          22